United States Patent [19]
Manghisi et al.

[11] 3,933,838
[45] Jan. 20, 1976

[54] 5-SUBSTITUTED 2-AMINO-4-ARYLTHIAZOLES

[75] Inventors: Elso Manghisi, Monza (Milan); Aldo Salimbeni; Giancarlo Fregnan, both of Milan, all of Italy

[73] Assignee: Instituto Luso Farmaco d'Italia S.r.l., Milan, Italy

[22] Filed: Feb. 23, 1973

[21] Appl. No.: 335,255

[30] Foreign Application Priority Data
Feb. 25, 1972  Italy .................................. 21086/72
Feb. 9, 1973  Italy .................................. 20231/73

[52] U.S. Cl. .................. 260/306.8 R; 260/247.1 M; 260/247.2 A; 260/268 C; 260/294.8 D; 260/299

[51] Int. Cl.² ................ C07D 277/46; C07D 277/42

[58] Field of Search .......... 260/306.8 R, 299, 294.8, 260/247.1

[56] References Cited
UNITED STATES PATENTS

| | | | |
|---|---|---|---|
| 2,423,709 | 7/1947 | Knott | 260/306.8 R |
| 3,575,991 | 4/1971 | Kim et al. | 260/306.8 R |

*Primary Examiner*—Richard J. Gallagher
*Assistant Examiner*—Diana G. Rivers
*Attorney, Agent, or Firm*—Flynn & Frishauf

[57] ABSTRACT

5-Substituted 2-amino-4-arylthiazoles have interesting properties as anti-inflammatories, antipyretics, analgesics, antibacterials, C.N.S. depressants, anti-ulcer, and anti-cough agents.

13 Claims, No Drawings

5-SUBSTITUTED 2-AMINO-4-ARYLTHIAZOLES

The present invention relates to a 2-amino-4-arylthiazole 5-substituted series, of interest in the field of pharmacology of the general formula (I):

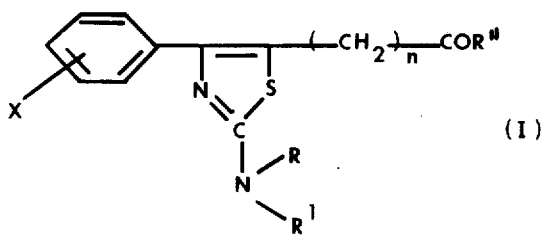

(I)

in which X represents hydrogen, halogen, hydroxy, lower alkoxy, lower alkyl or halogen-substituted lower alkyl, R and R' which are the same or different, represent hydrogen, lower alkyl, cycloalkyl, aryl (unsubstituted or substituted by halogen, hydroxy, lower alkoxy or lower alkyl), or aralkyl; alternatively, together with the nitrogen atom, they can form a saturated heterocyclic ring optionally containing other heteroatoms; while, when R represents hydrogen, R' may also represent —CO—R''', where R''' is hydrogen, alkyl, aryl, amino or arylamino; R'' represents hydroxy, —OR$^{IV}$, where R$^{IV}$ is straight or branched alkyl, hydroxyalkyl, aralkyl, aminoalkyl, or aminoalkoxyalkyl in which the amino group is primary or mono- or di-substituted by lower alkyl or is included in a heterocyclic ring (e.g. morpholine or pyrrolidine), or R'' represents

in which R$^V$ and R$^{VI}$, which may be the same or different, each represent hydrogen, straight, branched or cyclic lower alkyl, hydroxy-alkyl or aralkyl, aminoalkyl in which the amino group is primary or mono- or di-substituted by alkyl or is included in a heterocyclic ring, hydroxy, acyloxy or aryl either unsubstituted or substituted by alkyl or halogen; or the group:

$$-N\begin{matrix}R^V\\R^{VI}\end{matrix}$$

represents the residue of a heterocyclic amine (for instance, pyrrolidine, morpholine, piperazine, or N'-substituted-piperazine), and n represents 1, 2 or 3, provided that when R and R' both represent hydrogen, X is hydrogen, 4—Cl or 4—OCH$_3$, and n = 1, R'' is not hydroxy.

According to the invention, the compounds of formula (I) are obtained by the reaction of the compounds of formula:

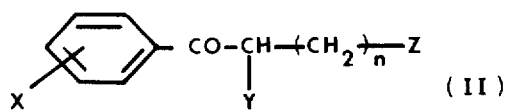

(II)

where X and n have the significance indicated above, Y represents hydroxyl, alkylsulphonyloxy, arylsulphonyloxy, or halogen and Z represents CN or COOH (which may be esterified with an aliphatic or aralphatic alcohol) with a thio-urea of formula:

(III)

where R and R' have the significance indicated above and, in the thiazole compound thus obtained, of formula:

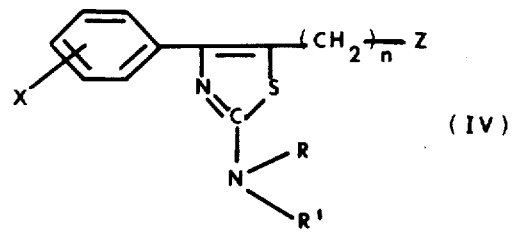

(IV)

changing the Z group (where Z is different from —COR''), in known manner into the COR'' radical.

According to a further feature of the invention, the compounds of formula IV are obtained by the reaction of formula (V) substances:

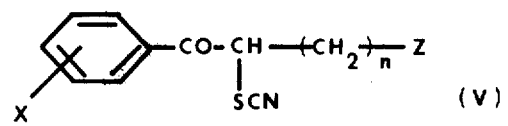

(V)

where X, n and Z have the significances specified above, with an amine of formula:

(VI)

where R and R' have the significances set out above, followed by changing the group Z (where Z is different from —COR'') in known manner into the COR'' radical.

According to a still further feature of the invention, the compounds of formula I are obtained by reacting a thiazole of formula:

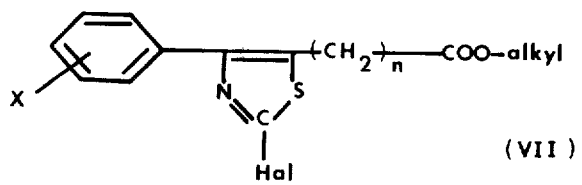

(VII)

where X and n have the significances already set out and Hal is chlorine or bromine, with an amine of formula (VI), followed, if desired, by transformation of the —COO—alkyl group into another radical of formula —COR".

According to yet another feature of the invention, the compounds of formula (I) in which R represents hydrogen and R' = —CO—R''' are prepared by reacting a compound of formula (I) in which both R and R' represent hydrogen, with an acid of formula R"λ'—COOH or a reactive derivative thereof (e.g. an acid halide, anhydride, or ester) or with phosgene followed by ammonia or an amine.

Among the known methods for the transformation of the Z and —COO—alkyl groups into different groups of formula —COR", suitable methods include the conventional methods for the transformation of esters or nitriles into acids (namely acid or alkali saponification) or of an ester into another ester (transesterification) and also the esterification of acids, the transformation of acids into their chlorides and subsequent reaction with amines, and the aminolysis of esters.

The intermediates are obtained by using known methods of synthesis; thus the compounds of formula (II), in which Y represents halogen, can be obtained by direct halogenation of the compounds in which Y=H.

Salts of the compounds of formula I containing a basic group can be prepared with pharmaceutically acceptable inorganic acids, e.g. hydrochloric, hydrobromic, nitric, sulphuric, and phosphoric acids, and organic carboxylic acids such as acetic, propionic, glycollic, malonic, succinic, maleic, hydroxymaleic, fumaric, malic, tartaric, citric, glucuronic, benzoic, mandelic, salicylic, 4-aminosalicylic, 2-phenoxybenzoic, pamoic, nicotinic, and isonicotinic acids, and organic sulphonic acids, for example methanesulphonic, ethanesulphonic, 2-hydroxyethanesulphonic, 1,2-ethanedisulphonic, p-toluenesulphonic, and naphthalene-2-sulphonic. Mono- or poly- salts are formed depending on the number of salifiable groups present in the molecule. Analogously, among the compounds of the formula I containing an acid group, pharmaceutically acceptable salts can be prepared with metals (such as sodium, potassium, calcium, magnesium, or aluminium) or with organic bases (such as morpholine, pyrrollidine, ethanolamine, or N,N-dibenzylethylenediamine).

The compounds of formula I and their salts have antiinflammatory, antipyretic, analgesic, antibacterial, C.N.S. depressant, anti-ulcer and anti-cough activities. They can be applied locally, taken by mouth or injected through appropriate pharmaceutical preparations in solid, liquid or suspension forms (e.g. as ointments, lotions, tablets, capsules, phials or elixirs).

The following Tables illustrate the pharmacological activities of some of the compounds of the invention, which are indicated in the Tables by the following code numbers:

LR 330 (2-phenylamino-4-p-chlorophenyl-thiazol-5-yl)-acetic acid
LR 331 (2-amino-4-p-chlorophenyl-thiazol-5-yl)-acetic acid
LR 364 [2-(phenylamino-carbonylamino)-4-p-chlorophenyl-thiazol-5-yl]-acetic acid
LR 396 [2-N-(2', 6'-dichlorophenyl)-amino-4-phenyl-thiazol-5-yl]-acetic acid
LR 407 (2-N,N-diethylamino-4-p-chlorophenyl-thiazol-5-yl)-acetic acid
LR 450 (2-amino-4-p-chlorophenyl-thiazol-5-yl)-N-(N',N'diethylaminoethyl)-acetamide.

The anti-inflammatory action has been studied in adult rats by using the carragenin oedema test (Proc. Soc. exp. Biol. Med. 1962, 111 : 544) and the granuloma from an extraneous substance (J. Amer. Pharm. Ass., Sci. Ed. 1957, 46 : 515).

The analgesic action has been assessed in rats (Arch. int. Pharmacodyn. 1957, 111 : 409) and in mice (Boll. Chim. Farm. 1968, 107 : 29), the antipyretic action in rats (J. Pharmacol. exp. Ther. 1963, 141 : 369); and the anti-cough action in guinea pigs made to inhale 4% ammonia.

The anti-ulcer property has been studied in rats kept without food for 24 hours and motionless for 4 hours (Therapie 1960, 15 : 1096).

Whenever possible the $ED_{50}$ values have been calculated.

| SUB-STANCE | $LD_{50}$ mg/kg. | | | | ANTI-INFLAMMATORY ACTION RATS | | ANTI-PYRETIC ACTION RATS | ANTI-COUGHING ACTION GUINEA PIGS |
|---|---|---|---|---|---|---|---|---|
| | MICE | | RATS | | $ED_{50}$ mg/kg. carrageenin oedema | granuloma | | |
| | intraperitoneal | oral | intraperitoneal | oral | intraperitoneal oral | oral × 7 days | $ED_{50}$ mg/kg/oral | $ED_{50}$ mg/kg/ intraperitoneal |
| LR 330 | >1000 | >3000 | >1000 | >2000 | 75  400 | 400 | *200 = φ | *200 = φ |
| LR 331 | 800 | >5000 | 840 | >1000 | 140  300 | 300 | *400 = φ | *50 = 17% |
| LR 364 | >1000 | | | | *200=φ | | | *200 = φ |
| LR 396 | >1000 | | | | *200=φ | | | |
| LR 407 | 400 | 1265 | 385 | >1500 | 60  120 | 170 | 73 | 34 |
| LR 450 | 43 | 238 | 47 | 915 | *6=36%  *100=35% | 100 | *100 = 38% | *12 = φ |

*maximum dose administered

| SUB-STANCE | LD$_{50}$ mg/kg | | | | ANALGESIC ACTION | | | ANTI-ULCER ACTION | |
|---|---|---|---|---|---|---|---|---|---|
| | MICE | | RATS | | Randall Selitto RATS ED$_{50}$ mg/kg/oral | Stretching acetic acid MICE ED$_{50}$ mg/kg/oral | Tail-clip MICE ED$_{50}$ mg/kg/oral | RATS 10 mg/kg/intraperitoneal | |
| | intra-peri-toneal | oral | intra-peri-toneal | oral | | | | Reduction in number of ulcers in % | Protected rats in % |
| LR 330 | >1000 | >3000 | >1000 | >3000 | 200 | 75 | *200 = φ | | |
| LR 331 | 800 | >5000 | 840 | >1000 | *175=15% | 132 | *175 = φ | 52 | 30 |
| LR 364 | >1000 | | | | | *200=31% | *200 = φ | 59 | 30 |
| LR 396 | >1000 | | | | | *100=26% | | 45 | 40 |
| LR 407 | 400 | 1265 | 385 | >1500 | >400 | 26 | 48 | 23 | |
| LR 450 | 43 | 238 | 47 | 915 | *100=18% | *100=27% | *50 = φ | 69 | 65 |

*maximum dose administered.

All the products obtainable according to the present invention are new except the following: (2-amino-4-phenyl-thiazol-5-yl)-acetic acid, (2-amino-4-parachlorophenyl-thiazol-5-yl)-acetic acid, (2amino-4-anisyl-thiazol-5yl)-acetic acid, and their respective ethyl esters, which are mentioned in the U.S. Pat. No. 2,423,709, where, however, no mention is made of the pharmacological properties of these compounds.

The Examples given below illustrate the invention without however limiting it. The melting and boiling points are not corrected. The identity of the substances and their purity have been checked by elementary analysis of C, H and N (and halogens when present), infrared spectra, N.M.R. and U.V.

EXAMPLE 1

(2-Amino-4-para-fluorophenyl-thiazol-5-yl)-acetic acid (hydrobromide)

A mixture of 10 grams of β-bromo-β-p-fluorobenzoyl-propionic acid and 2.77 grams of thio-urea in 60 c.c. of isopropyl alcohol is refluxed for 1 hour. After cooling, the precipitated solid is filtered off and recrystallised from isopropyl alcohol, m.p. 267°–268°C.

In the same way:
(2-Amino-4-p-methoxyphenyl-thiazol-5-yl)-acetic acid (hydrobromide, m.p. 258°-259°C.), and [2-N-(2',-6'-dichlorophenyl)-amino-4-phenyl-thiazol-5-yl]-acetic acid (m.p. 278°–80°C.) can be prepared.

EXAMPLE 2

Ethyl-(2-N-phenylamino-4-p-chlorophenyl-thiazol-5-yl)acetate.

A mixture of 8.4 g. of ethyl β-bromo-β-p- chlorobenzoylpropionate and 4 grams of phenylthio-urea in 30 c.c. absolute alcohol is refluxed for 8 hours. The alcohol is removed in a vacuum and the residue is treated with 50 c.c. of H$_2$O and 100 c.c. of diethyl ether. It is made alkaline with Na$_2$CO$_3$ and the organic phase is separated, washed several times with H$_2$O, dried over Na$_2$SO$_4$ and evaporated to dryness. The residue is recrystallised from isopropyl alcohol, m.p. 120°–121°C.
In the same way, the following can be prepared. Ethyl-[2-N-(2',6'-dichlorophenyl)-amino-4-p-chlorophenyl-thiazol-5-yl]-acetate (m.p. 192°–193°C.),
ethyl-(2-amino-4-p-chlorophenyl-thiazol-5-yl)-acetate (m.p. 156°–157°C.), and
ethyl-3-(2-amino-4-p-chlorophenyl-thiazol-5-yl)-propionate (m.p. 160°–161°C.) are prepared in the same way.

EXAMPLE 3

(2-Phenylamino-4-p-chlorophenyl-thiazol-5-yl)-acetic acid.

7 grams of ethyl (2-N-phenylamino-4-p-chlorophenyl-thiazol-5-yl)acetate are heated to reflux with 20 c.c. of 5% NaOH for 1 hour. It is neutralised with N HCl. The precipitated solid is filtered and washed several times with H$_2$O. M.p. 256°–57°C.

In the same way the following can be prepared:
(2-acetylamino-4-p-chlorophenyl-thiazol-5-yl)acetic acid (m.p. 270°–73°C. from isoamyl alcohol).
[2-N-(2',6'-dichlorophenyl)amino-4-p-chlorophenyl-thiazol-5-yl]-acetic acid (m.p. 270°–71°C.).
(2-Amino-4-phenyl-thiazol-5-yl)-acetic acid (m.p. 232°–34°C.).
(2-Amino-4-p-chlorophenyl-thiazol-5-yl)-acetic acid (m.p. 262°–63°C.).
3-(2-Amino-4-p-chlorophenyl-thiazol-5-yl)propionic acid (m.p. 206°–07°C.). [2-(Phenylaminocarbonylamino)-4-p-chlorophenyl-thiazol-5-yl]-acetic acid (m.p. 212°–214°C., from dioane – H$_2$O).
(2-Diethylamino-4-p-chlorophenyl-thiazol-5-yl)-acetic acid (m.p. 132°–33°C.).

EXAMPLE 4

[2-(N,N-diethylamino)-4-p-chlorophenyl-thiazol-5-yl]-ethyl acetate.

6 grams of ethyl (2-hydroxy-4-p-chlorophenyl-thiazol-5-yl)-acetate and 20 c.c. of POCl$_3$ are refluxed for 1 hour. The excess of POCl$_3$ is eliminated in a vacuum and the residue is treated with an excess of diethylamine. After 24 hours H$_2$O is added and the mixture is extracted several times with ether. The ether solution is separated, dried over Na$_2$SO$_4$, and evaporated to dryness. The residue is crystallised from 95% alcohol, m.p. 55°-56°C.

The starting material can be prepared as follows: 23 grams of ethyl β-bromo-β-p-chlorobenzoyl-propionate and 7.5 grams of ethyl thiocarbamate in 100 c.c. isopropyl alcohol are refluxed for 30 minutes. After cooling the precipitated solid is filtered off and recrystallised from 95% alcohol, m.p. 153°–54°C.

EXAMPLE 5

Ethyl (2-acetylamino-4-p-chlorophenyl-thiazol-5-yl)acetate.

A mixture of 13.4 grams of ethyl (2amino-4-p-chlorophenyl-thiazol-5-yl)acetate and 10.2 grams of acetic anhydride in 50 c.c. of anhydrous pyridine is refluxed for ½ an hour. The solution is poured on ice. The precipitated solid is filtered off, washed several times with H₂O, and recrystallised from 80% alcohol, m.p. 187°–88°C.

EXAMPLE 6

Ethyl [2-(phenylaminocarbonylamino)-4-p-chlorophenyl-thiazol-5-yl]-acetate.

2 Grams of phenylisocyanate in 50 c.c. ether are added to a suspension of 5 g. of ethyl (2-amino-4-p-chlorophenyl-thiazol-5-yl)-acetate in 200 c.c. of anhydrous ether. After 24 hours the precipitated solid is filtered off, m.p. 192°–93°C.

EXAMPLE 7

(2-Amino-4-p-chlorophenyl-thiazol-5-yl)-N-(N',N'-diethylaminoethyl)-acetamide.

6 g. of ethyl (2-amino-4-p-chlorophenyl-thiazol-5-yl)-acetate are added tp 7.7 g. of N,N-diethylethylenediamine in which 50 mg. of metallic sodium have been dissolved. The mixture is heated under nitrogen until all the alcohol released by the reaction has distilled (3 hours). The excess of amine is eliminated in a vacuum. The residue is treated with H₂O and extracted several times with ether. After drying over Na₂SO₄, the solvent is eliminated in a vacuum. The residue is recrystallised from benzene, m.p. 113°–114°C.

We claim:

1. A 5-substituted 2-amino-4-arylthiazole of the formula

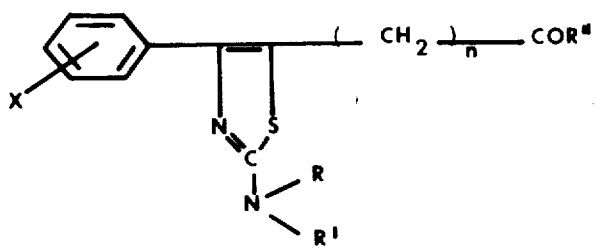

in which X represents hydrogen, halogen or methoxy; R is hydrogen or ethyl; R' is phenyl unsubstituted or substituted with halogen, and when R is hydrogen, R' can be —CO—R''', where R''' is methyl or phenylamino; R'' is hydroxy, ethoxy or 2-diethylaminoethylamino, and n is 1, 2 or 3.

2. [2-N-(2', 6'-dichlorophenyl)-amino-4phenyl-thiazol-5-yl]-acetic acid and pharmaceutically acceptable salts thereof.

3. Ethyl(2-N-phenylamino-4-p-chlorophenyl-thiazol-5-yl)-acetate and pharmaceutically acceptable salts thereof.

4. Ethyl[2-N-(2', 6'-dichlorophenyl)-amino-4-p-chlorophenyl-thiazol-5-yl]-acetate and pharmaceutically acceptable salts thereof.

5. (2-Phenylamino-4-p-chlorophenyl-thiazol-5-yl)-acetic acid and pharmaceutically acceptable salts thereof.

6. (2-Acetylamino-4-p-chlorophenyl-thiazol-5-yl)-acetic acid and pharmaceutically acceptable salts thereof.

7. [2-N-(2',6'-dichlorophenyl)amino-4-p-chlorophenyl)-thiazol-5-yl]-acetic acid and pharmaceutically acceptable salts thereof.

8. [2-(Phenylaminocarbonylamino)-4-p-chlorophenyl-thiazol-5-yl]-acetic acid and pharmaceutically acceptable salts thereof.

9. (2-Diethylamino-4-p-chlorophenyl-thiazol-5-yl)-acetic acid and pharmaceutically acceptable salts thereof.

10. Ethyl[2-(N,N-diethylamino)-4-p-chlorophenyl-thiazol-5-yl]-acetate and pharmaceutically acceptable salts thereof.

11. Ethyl(2-acetylamino-4-p-chlorophenyl-thiazol-5-yl)-acetate and pharmaceutically acceptable salts thereof.

12. Ethyl[2-(phenylaminocarbonylamino)-4-p-chlorophenyl-thiazol-5-yl]-acetate and pharmaceutically acceptable salts thereof.

13. (2-Amino-4-p-chlorophenyl-thiazol-5-yl)-N-(N',N'-diethylaminoethyl)-acetamide and pharmaceutically acceptable salts thereof.

* * * * *